United States Patent
Chan et al.

(10) Patent No.: US 9,835,542 B2
(45) Date of Patent: Dec. 5, 2017

(54) OPTICAL BLOCK

(71) Applicant: DNA Medicine Institute, Inc., Cambridge, MA (US)

(72) Inventors: Eugene Y. Chan, Cambridge, MA (US); Julia Z. Sharpe, Cambridge, MA (US)

(73) Assignee: DNA Medicine Institute, Inc., Cambridge, MA (US)

(*) Notice: Subject to any disclaimer, the term of this patent is extended or adjusted under 35 U.S.C. 154(b) by 249 days.

(21) Appl. No.: 14/574,282

(22) Filed: Dec. 17, 2014

(65) Prior Publication Data

US 2015/0177120 A1 Jun. 25, 2015

Related U.S. Application Data

(60) Provisional application No. 61/916,998, filed on Dec. 17, 2013.

(51) Int. Cl.
| | |
|---|---|
| *H01L 27/00* | (2006.01) |
| *G01N 15/14* | (2006.01) |
| *G01N 21/01* | (2006.01) |
| *G01N 21/05* | (2006.01) |

(52) U.S. Cl.
CPC ........ *G01N 15/1434* (2013.01); *G01N 21/01* (2013.01); *G01N 21/05* (2013.01); *G01N 15/1459* (2013.01)

(58) Field of Classification Search
CPC . G01N 15/1434; G01N 15/1436; H01L 31/16
USPC .................. 250/216, 221, 239; 362/257, 259
See application file for complete search history.

(56) References Cited

U.S. PATENT DOCUMENTS

| 6,042,249 A * | 3/2000 | Spangenberg | G01N 15/14 362/259 |
| 2004/0062685 A1* | 4/2004 | Norton | G01N 15/14 422/81 |

\* cited by examiner

*Primary Examiner* — Kevin Pyo
(74) *Attorney, Agent, or Firm* — Danielson Legal LLC (57) ABSTRACT

An integrated optical block that is highly portable and compact, designed to measure cells and particles.

12 Claims, 12 Drawing Sheets

OPTICAL BLOCK

CROSS-REFERENCE TO RELATED APPLICATIONS

The present application claims the benefit of U.S. provisional application No. 61/916,998, filed on Dec. 17, 2013, the entire disclosure of which is incorporated by reference as if set forth in its entirety herein.

TECHNICAL FIELD

The present invention generally relates to an optical block for measuring optical signals and, more specifically, to a monolithic optical block that measures optical signals from particles in a fluid channel.

BACKGROUND

Precise biomedical measurements are possible in a wide variety of settings, such as central hospital laboratories, medical offices, and emergency rooms. These measurements typically use large analyzers that can weigh several hundred pounds and require significant technical support.

In contrast, point-of-care tests often lack the analytical sensitivity of larger analyzers. Lateral flow tests are used frequently in point-of-care settings and these tests typically have a readout of two lines: a control and a test line. These are read by visual inspection, yielding a qualitative answer. The nature of the readout prevents these types of tests from attaining high sensitivity and quantitative determination of analyte concentration.

It is therefore highly desirable to have improved instrumentation available at the point-of-care for accurate, precise, and quantitative measurements of various analytes.

SUMMARY

Embodiments of the present invention relate to an optical system that is designed in such a way that lasers, detectors, flow channel, lenses, and electronics can be readily affixed to their precise locations in an optical block with minimal effort. In order to accomplish this, embodiments of the invention utilize precise methods and locations within the optical block to enable a full assembly of a complex laser-based optical system with minimal effort.

In one aspect, to shorten the focal lengths of the lenses utilized in the system, a diverging cylindrical lens approach is taken. The laser beam is incident upon the diverging lens or lenses, then focused through an achromat, then onto a small channel. One advantage of this format is that the optics can fit into a highly confined space, limited only by the focal length of the focusing lens which can be any type of lens including achromat, plano-convex, double convex, aspheric, etc.

In another aspect, the fluid channel is securely and readily integrated into the system. Without the channel, biological samples cannot be analyzed by the system. The integration of the channel into the system is a potential difficulty since the channel is only tens to hundreds of microns. Since the laser spot needs to be directed into the channel, the channel needs to be secure and fixed in place without need for adjustment and realignment. Embodiments of the optical block have integrated passive or active positioning mechanisms to allow for precise location of the channel in the system.

In still another aspect, embodiments of the present invention include a means for controlling sample flow within the channel, including either performing 1D or 2D flow-focusing. By utilizing unique geometries within the optical block, focused flows can be attained within the channel. Conventional methods to focus flows are large because they require macroscopic fittings, large bore tubing, and a sizeable funnel and pin assembly for focusing flows. Embodiments of the present invention utilize hypodermic needle gauge ports to replace the larger fittings and another hypodermic needle gauge to direct the sample into the channel. This 2D flow focusing method is integrated into the optical block, allowing for consistent optical system performance.

In yet another aspect, embodiments of the present invention have a filter assembly with a removable filter block. In one embodiment, the optical block has a filter block that mates with a three-point positioning system to allow removal and reattachment of the filter block.

In one aspect, small area solid-state detectors, selected from avalanche photodiodes and silicon photomultipliers, are attached to the filter block. The small area of the solid-state detectors is utilized to significant advantage, in that they act as both pinholes and detectors simultaneously. Conventional large area detectors require an accessory pinhole and this requires more space within the confines of the optical block. The use of solid-state detectors dramatically decreases their size, and when the size of the detector is matched to the desired image size, then effective confocal detection is attained and the result is a high-performance optical system.

In another aspect, the optical block module has drop in positions for the electrical board and this allows for close proximity of the electrical components to the detectors. Using semi-circle soldering ports on the printed circuit board (PCB), the electrical leads on the detectors are directly soldered and connected to the PCB for low-noise electrical connection that improves the performance of the optical block.

In one embodiment, the invention relates to an optical block having a body fabricated from a rigid material, at least one optical component located within the body, wherein each of the at least one optical components is mounted in the body using a registration feature.

In one embodiment, the rigid material is aluminum, such as black anodized aluminum or partially-anodized aluminum. In one embodiment, the at least one optical component is selected from the group consisting of a laser, a filter, a focusing lens, a flow channel, and a detector. In one embodiment, the registration feature is selected from the group consisting of three point alignment machined directly into the body, posts designed into the body, cylindrical ports designs into the body, and registration features on the body. In one embodiment, the optical block is approximately the size of a matchbox.

In one embodiment, the block has two lenses, and one of the lenses is a diverging cylindrical lens and the other lens is selected from the group consisting of a focusing achromatic lens, an aspheric lens, a plane convex lens, and a double convex lens. In another embodiment, the block has two cross-cylindrical diverging lenses and a focusing lens.

In one embodiment, the block has tubing connection ports fabricated from hypodermic tubing. In one embodiment, the block has a sample tube port, a sheath tube port, and a burp tube port. In one embodiment, the block includes a solid-state detector. In one embodiment, the solid-state detector is soldered directly to an electronics board. In one embodiment, the optical block lacks a pinhole in proximity to the solid-state detector.

In one embodiment, the block further includes an integrated heat sink.

It is to be understood that the invention is not limited in its application to the details of the construction and arrangement of parts illustrated in the accompanying drawings and discussed herein below. The invention is capable of other embodiments and of being practiced or carried out in a variety of ways. It is to be understood that the phraseology and terminology employed herein are for the purpose of description and not of limitation.

BRIEF DESCRIPTION OF DRAWINGS

Non-limiting and non-exhaustive embodiments are described with reference to the following Figures in which.

In the drawings, like reference characters generally refer to corresponding parts throughout the different views. The drawings are not necessarily to scale, emphasis instead being placed on the principles and concepts of operation.

DETAILED DESCRIPTION

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions that could be embodied in software, firmware or hardware, and when embodied in software, could be downloaded to reside on and be operated from different platforms used by a variety of operating systems.

In addition, the language used in the specification has been principally selected for readability and instructional purposes and may not have been selected to delineate or circumscribe the inventive subject matter. Accordingly, the disclosure of the present invention is intended to be illustrative, but not limiting, of the scope of the invention, which is set forth in the claims.

Overview

One of the best ways to obtain high sensitivity measurements is through the use of lasers for analysis of cells and particles in a flowing stream. Coupled with the appropriate optics and sensitive detectors, precision measurements can be obtained in a reasonable manner. Current approaches, however, require large optical systems in order to achieve the desired performance levels. The ability to implement these optical systems in a compact, portable, and high-sensitivity setting is desirable.

One of the major challenges is that laser-based optical systems require precise alignment. Bench-based optical systems require positioning devices that are have multiple axes and multiple alignment knobs. A single positioning mount can be the size of an entire point-of-care device. This makes developing a small, point-of-care, optical system exceptionally challenging, particularly in light of the precision alignment required for focusing the light onto the flow channel and then also collecting the light onto the detectors. The alignment needs to be stable over time and be robust with respect to shock and vibration.

Conventional optical paths for precision laser systems are long. This poses an inherent problem when designing a matchbox-sized system. The long optical path is a result of the long focal length lenses required to arrive at the desired beam and spot quality for precision biological measurements. Similarly, there are long optical paths that are necessary for guiding light into the detectors. In most laser-based detection systems, there are infinity detection optics that allow for stacking of multiple dichroic filters and optical elements. Being able to have compact optics is a prerequisite in being able to arrive at a small, precision, laser-based optical system.

Conventional methods utilize long focal length converging cylindrical lenses to generate a laser line on the flow channel. These long focal lengths cannot be utilized in a compact optical system. In order to get appropriate beam shaping in two dimensions two different converging lenses are typically utilized on a circular laser spot, resulting in an elliptical laser spot that has advantages of uniformity and cell or particle transit time. The short axis of the elliptical spot is typically aligned such that it is in the direction of the flow. The long axis spans the channel and provides for uniform illumination across the center of the channel.

The fluidic assembly in the optical block needs to accommodate a small flow channel so that biological samples, cells, and particles can pass through in a ready manner. Conventional fluidic assemblies, ports, and fittings are large. A conventional flow channel assembly would be the size of a point-of-care device. Significant reduction in the size of the fluidics attachment is a must and ideally, the fluidics attachments are integrated into the optical block. Geometrical positioning of the flow channel assembly is particularly important since this directly relates to the alignment of the system.

At times, it is highly desired that the flow in the channel be flow focused in one or two dimensions. Since fluid flows have parabolic flow profiles in small channels, the flow is the fastest in the center of the channel. Ideally, the sample flow would be confined to the center of the channel for the most uniform flow profile. Conventionally, flow focusing mechanical assemblies are utilized to accomplish this objective. Unfortunately, these flow assemblies are large, consume significant fluid, have large fittings, and are generally incompatible with a small, compact point-of-care device. Any miniaturized flow assembly needs to have precision, stable flows over time that are consistent with high performance analytical measurements.

For a miniature optical block module, it may be important that the filters be removable and readily interchanged. Given the small nature of the optical block, the removal and insertion of the filters can be problematic. Special alignment features are needed to maintain precise positioning from filter to filter. The alignment should be drop-in so that the filters or filter block can be swapped readily without hassle. This is particularly important for small biomedical research instrumentation where different filter sets may be important and highly desired. The alignment method should account for the various tolerances of the components to ensure that parts can be readily interchanged.

Conventional high sensitivity optical systems utilize large area detectors that are expensive, delicate, and subject to photocathode degradation. One such type of detector is the photomultiplier tube. It is impractical that these types of detectors be utilized for the application. Solid-state detectors are more desirable. Generally, the performance characteristics of these types of detectors are different, including gain, dynamic range, and operating voltage. While the ability to utilize solid-state detectors in a compact system is highly desired, they need to be connected in a low-noise manner that optimizes the optical signal coming from the cells or particles in the channel.

The ability to address these various challenges will result in a highly effective approach for a highly compact, precise optical system that is suitable for field portable applications. This will allow for lab quality data for a variety of different settings including space, hospital, ambulance, third world, military, and consumer applications. Instead of qualitative results, as measured by conventional lateral-flow assays, the use of a precision, compact optical system will allow for high analytical sensitivity, precise measurements, and robust reproducibility.

Open Air Optical Block

In a first embodiment, the optical block is designed to be an open air format where the optical components can be readily mounted from the top of the optical block. The optical block is made of a rigid material, ideally black anodized aluminum. In this manner, the optical components remain in alignment over time. The open air format allows the lasers, filters, focusing lenses, flow channel, detectors, and other optical components to be readily assembled and manufactured easily.

The open air optical block utilizes several means of aligning the optical components. Three point alignment is utilized for registration of some of the components. This approach is important since the components need to be precisely positioned. In the case of the first embodiment, the three point alignment is machined directly into the block. The optical block also utilizes posts for mounting of filter components. The posts are designed into the optical block. The optical components are directly mounted to the posts, allowing for precise positioning. Registration features on the optical block allow for placement of the focusing lenses. The features allow the lenses to be readily focused in the axis of the lens. The flow channel area has either a ported registration area or a three point alignment area. The seal around the flow channel is made by screwing a lid over the top of the flow channel. This approach allows for exacting placement of the flow channel within the optical block. Other registration features on this embodiment of the optical block include curved surfaces (i.e. for laser positioning).

The size of this embodiment may be as small as 2.4"× 1.5"×0.4". This is about the size of a matchbox. This provides significant portability and capabilities in a small volume. In order to fully fit all the components onto this particular embodiment, the optics need to be different. The focusing lenses for the lasers include at least one diverging cylindrical lens paired with a focusing achromatic, aspheric, plane convex, double convex, or other type of focusing lens. In the case of the one cylindrical lens, it serves to elongate the laser beam in one dimension, creating a laser line at the flow channel. This serves to increase the uniformity of the laser illumination. In conventional optical systems of this type, converging cylindrical lenses with positive focal lengths are utilized. This creates a significant limitation to the size of the optical block. For instance, if the focal length is +8.0" then, the optical block would at least be that size. Conversely, the use of a −8.0" lens would fit well in our current optical block, especially when paired with a positive focal length focusing lens. In this configuration, the positive focal length focusing lens can be 0.5" or have a similar short focal length to allow projection of the laser onto the flow channel. In the case where an elliptical laser spot is desired at the flow channel, the use of cross cylindrical diverging lenses can be utilized. This allows for beam shaping in both axes. The final size of the elliptical spot is dependent on the ratio of the two negative focal lengths for the diverging cylindrical lenses. The lenses can be anti-reflection coated. The use of an achromat as the focusing lens allows two different laser wavelengths to be utilized. The laser beam shaping lens in our optical block is thus one of the reasons that the system can be compact.

The flow channel area in the first embodiment minimizes the size of the fluidic connection ports and thus the overall flow channel region. Instead of conventional connectors, ports, and fittings, this embodiment utilizes hypodermic tubing, between 23 gauge to 28 gauge, as connectors. This dramatically minimizes the size of the tubing connected to the hypodermic tubing. The flow channel is mounted directly into registration features in the optical block. Furthermore, the flow cell top, comprised of the hypodermic tubing, has registration features that mate directly with registration features on the optical block. 0-80 screws clamp the top down onto the flow channel area, allowing a fluid seal for the flow channel. The flow cell top has three different ports: sample tube, sheath tube, and burp tube. The sample enters through the sample tube and then it is flow-focused by the sheath. For occasional clearing of bubbles or priming the system, the burp port is utilized.

The detectors utilized in the embodiment are solid-state detectors based on silicon. The advantage of these is that it allows the detection element to be packaged into a small form factor, such as a TO-18 can or similar type of form factor. The solid-state detectors have several requirements: high gain, appropriate spectral response, and good dynamic range. Conventional optical systems with high sensitivity utilize photomultiplier tubes (PMTs). PMTs are large area detectors that require a pinhole in front of it to spatially filter the light at the image plane. This introduces an additional optical element which increases the complexity of the system. In our embodiment, we utilize the small area of the solid state detector as the effective image plane pinhole to spatially filter the signal. This obviates the need for the additional optical element. By using the small area of the solid-state detector at the image plane, effective confocal performance can be attained, thus rejecting out-of-plane light for best and most optimal signal-to-noise in the system.

The electronics board is positioned in close proximity to the detectors. The leads on the TO-18 can be bent down and directly soldered into the electrical board. The printed circuit board (PCB) has semi-circle soldering pads for direct soldering of the leads to the PCB. The semi-circle soldering pads fully enable this configuration to be possible.

Figure 1:
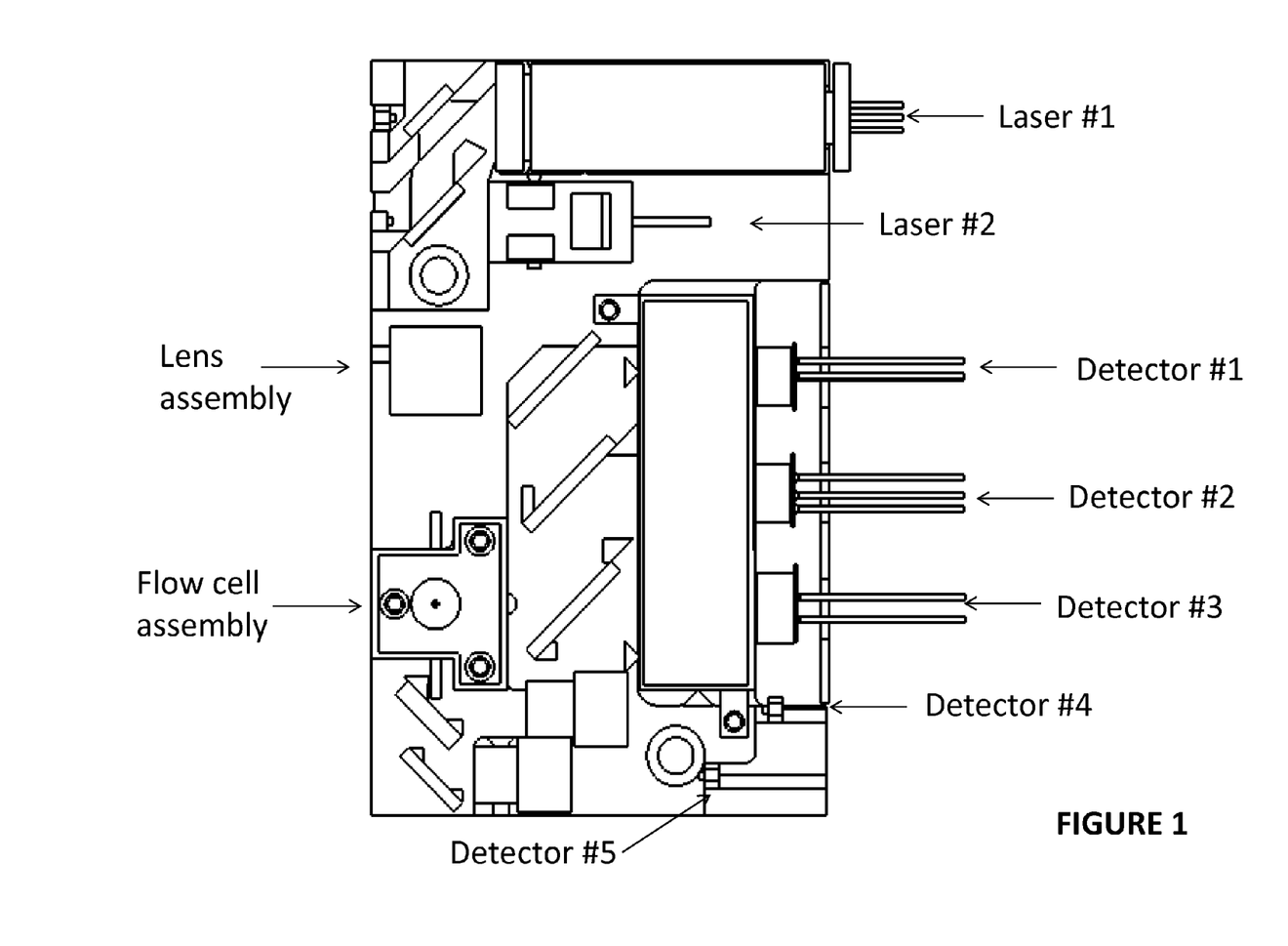
FIG. 1 is a top view of a first embodiment of the optical block.

FIG. 1 shows a top view of the optical block with the assembled components including the lasers, filters, laser focusing lens, flow channel area, and lens filter assembly with detectors. The design of the block allows for ready integration and large-scale manufacturing.

Figure 2:
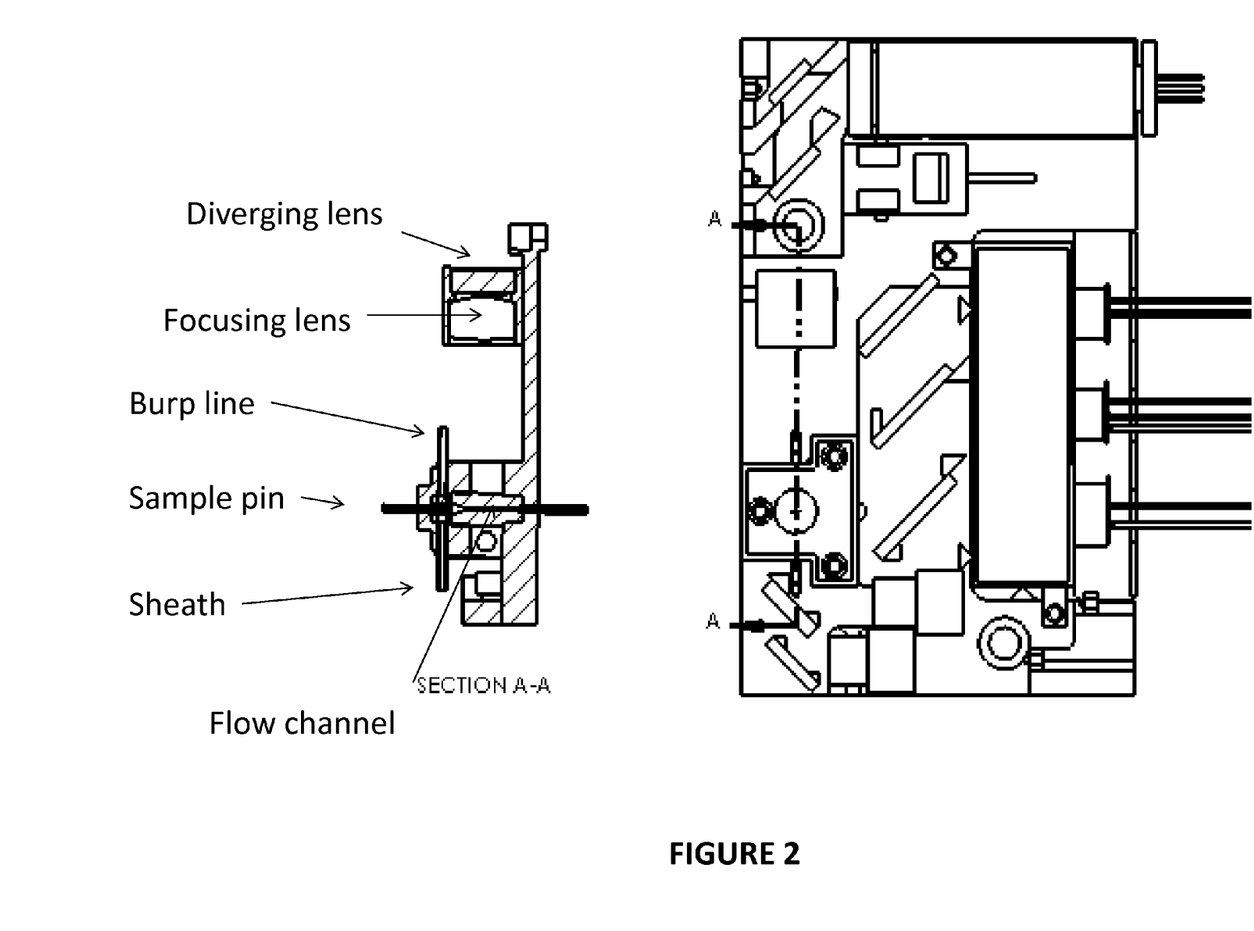
FIG. 2 is the view of FIG. 1 with a cutout to show interior detail.

FIG. 2 shows the view of FIG. 1 with a section cut-out. The section view shows the objective lens area detail and the flow channel area. The objective lens is utilized to create a uniform laser spot in the channel. It includes at least one cylindrical diverging lens coupled with a focusing lens to generate an high-uniformity elliptical laser spot in the flow channel. The flow channel area comprises the sample pin, burp line, and sheath flow channel.

Figure 3:
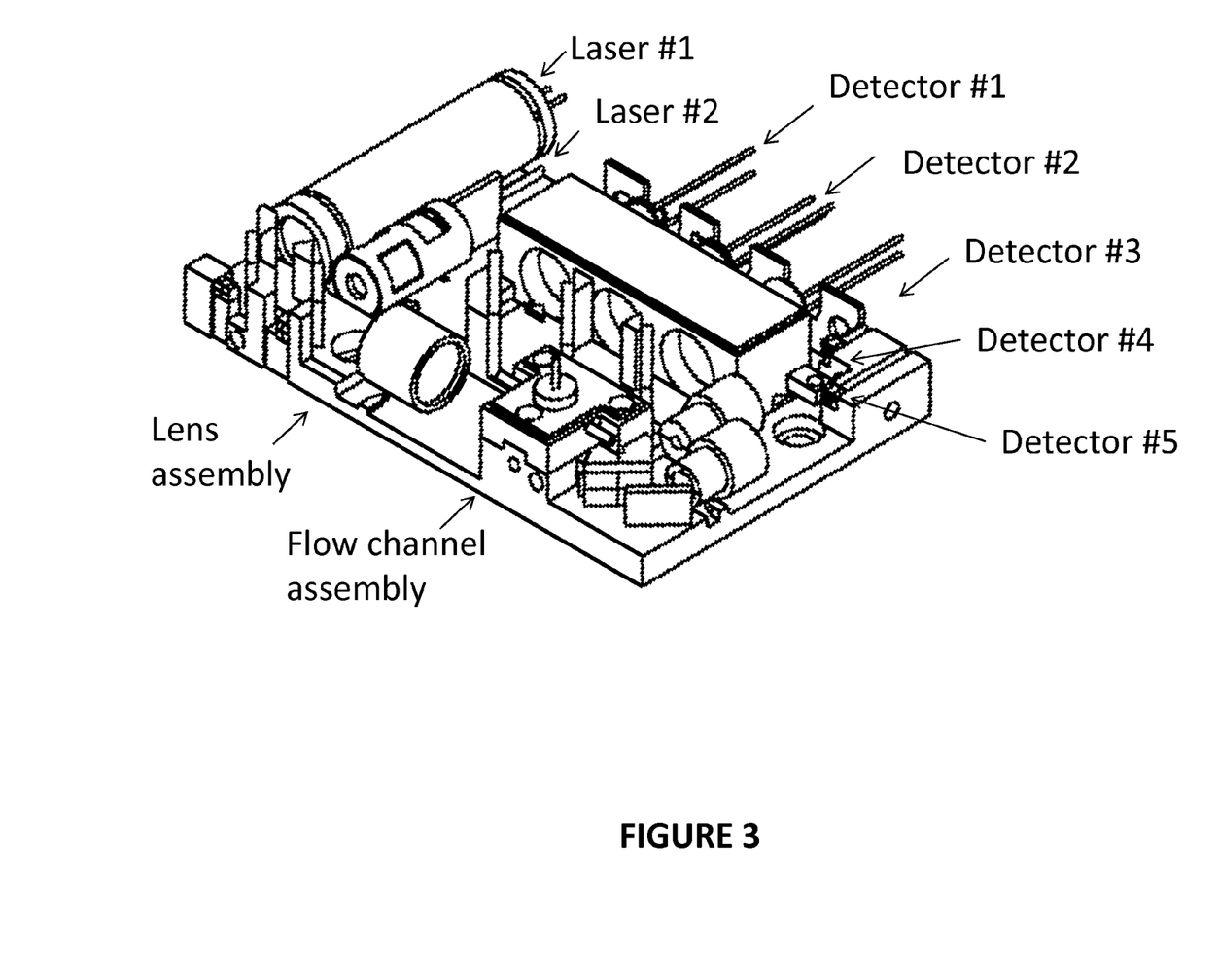
FIG. 3 is an isometric view of the fully assembled first embodiment of the optical block.

FIG. 3 shows the isometric view of a fully assembled optical block. This includes the two lasers, lens assembly, flow channel assembly, various detectors, filters, and the lens-filter assembly.

Figure 4:
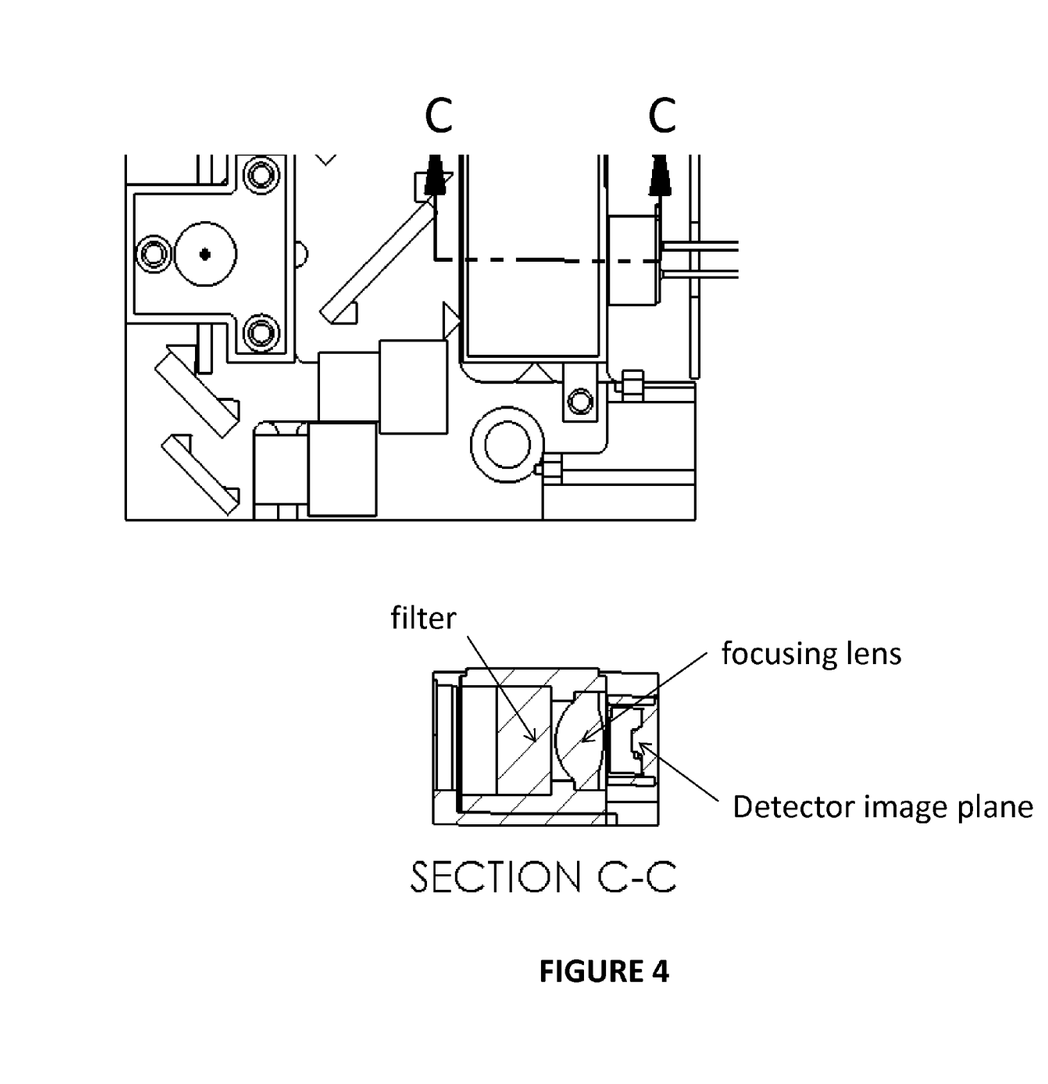
FIG. 4 is a partial top view of the first embodiment of the optical block and also a section view of the lens filter assembly.

FIG. 4 shows a partial top view of the optical block and also a section view of the lens filter assembly. The section view shows a sequence of filter, focusing lens, and detector. There is no pinhole in the system since the detector image plane is utilized as the effective pinhole. This configuration obviates the need for the pinhole and additional optics associated with such a configuration.

Figure 5:
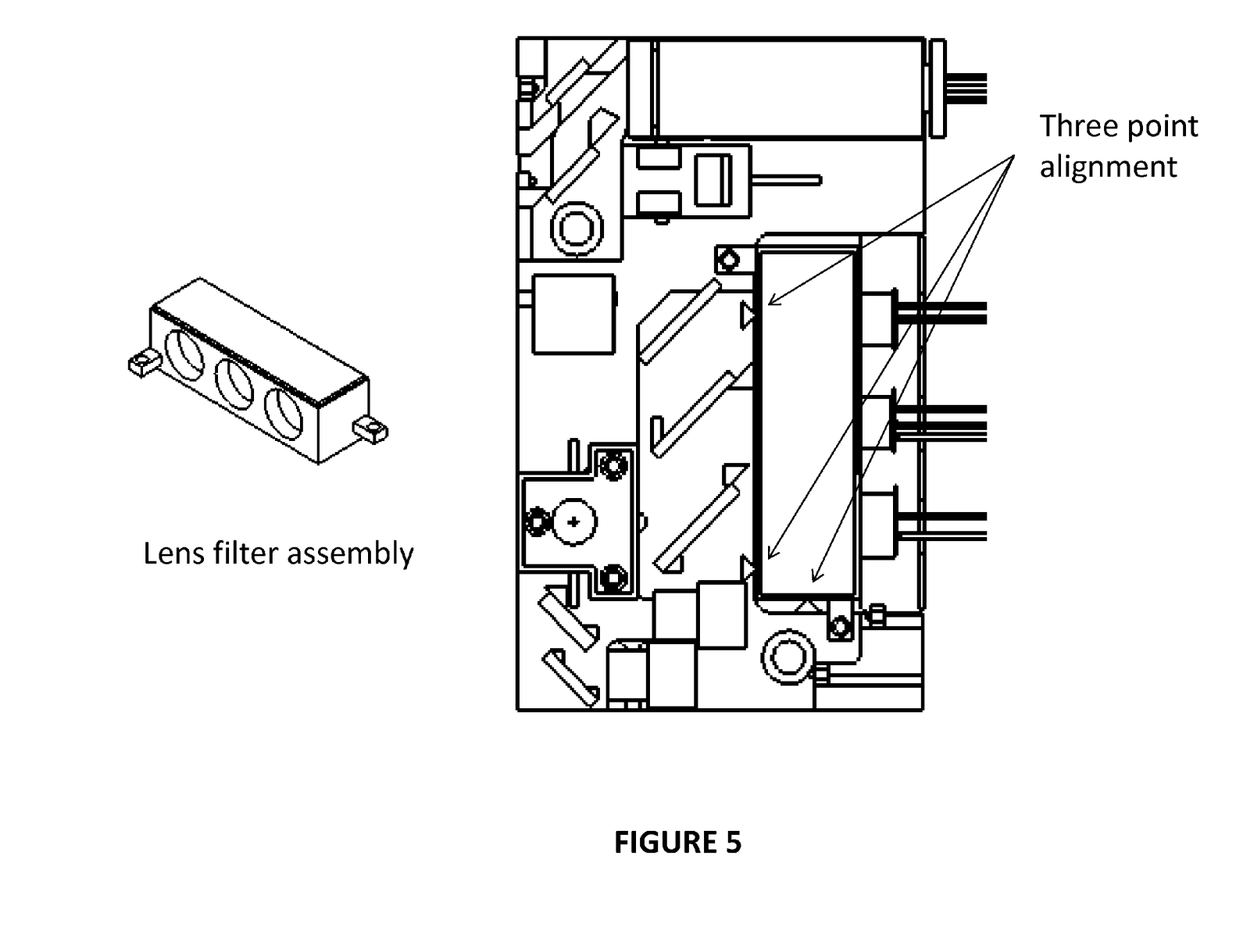
FIG. 5 shows a removable lens filter assembly that has three-point alignment with the rest of the optical block.

FIG. 5 shows a removable lens filter assembly that has three-point alignment with the rest of the optical block. The three point positioning allows rapid alignment of the lens filter assembly with the rest of the optical components on the block.

Figure 6:
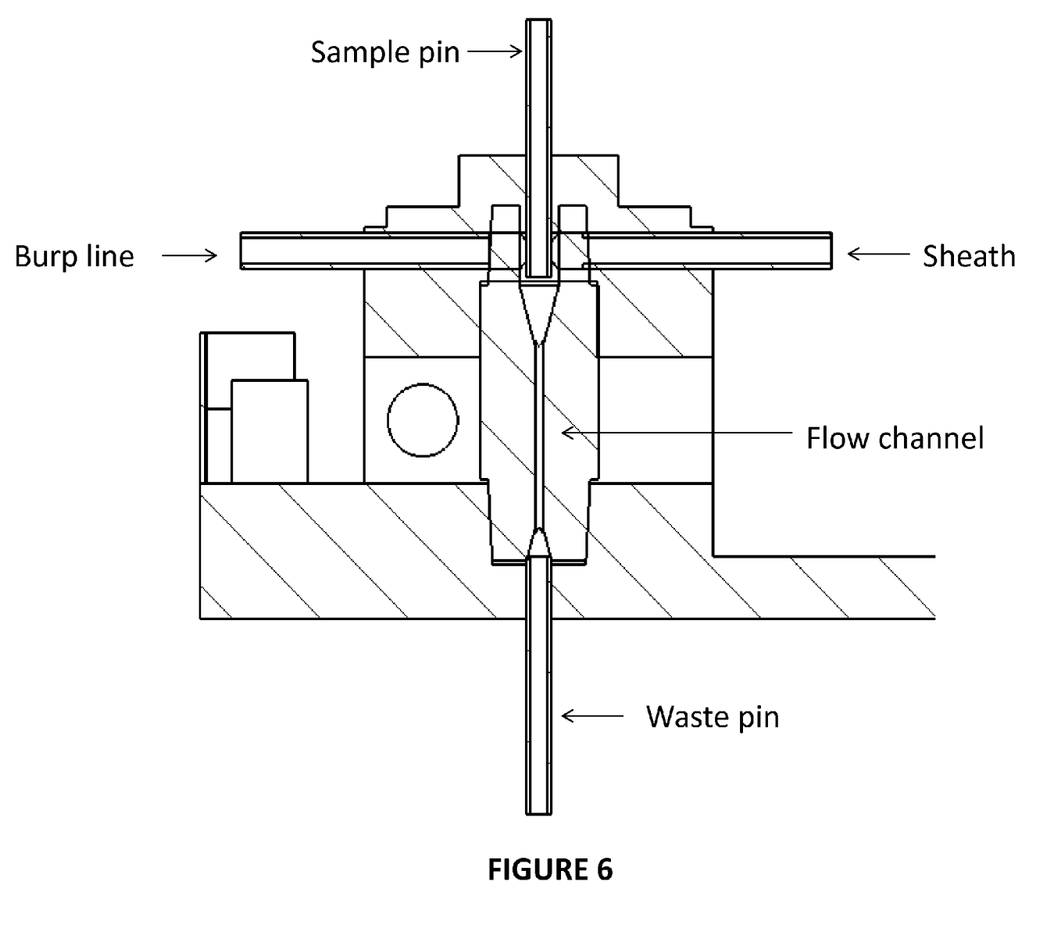
FIG. 6 is an enlarged section view of the main flow channel area.

FIG. 6 shows an enlarged section view of the main flow channel area. In contrast to conventional flow channel areas, which are large and utilize macroscopic fittings, the optical block utilizes hypodermic tubing to mate with a miniature flow channel top and flow channel exit port. The optical block has registration features that allow for precise location of the flow channel in the optical block.

Figure 7:
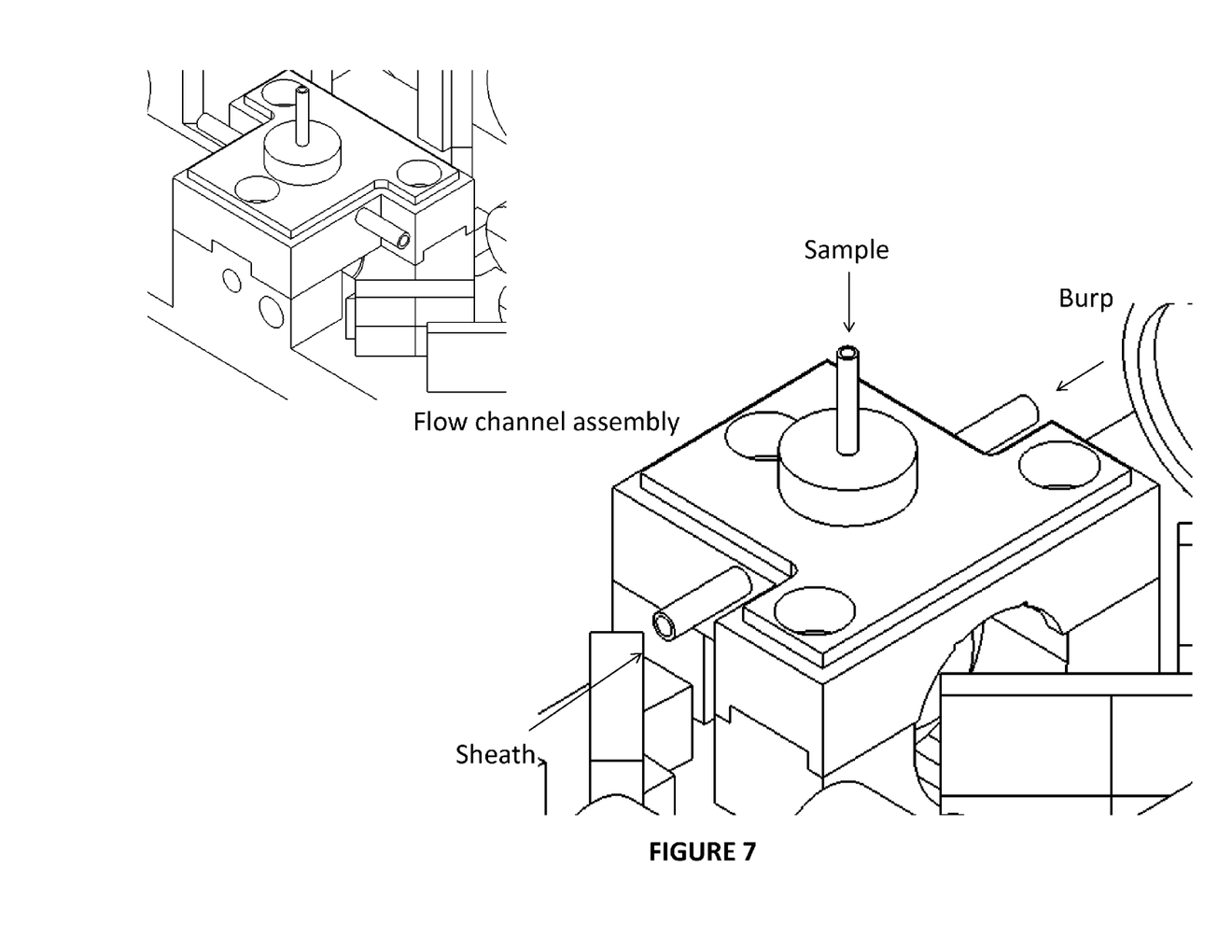
FIG. 7 is a detailed isometric view of the flow channel area top.

FIG. 7 shows a detailed isometric view of the flow channel area top. The sample inlet port is at the top and the burp and sheath ports are on the sides. The registration features allow precise relative positioning of the flow channel.

Figure 8:
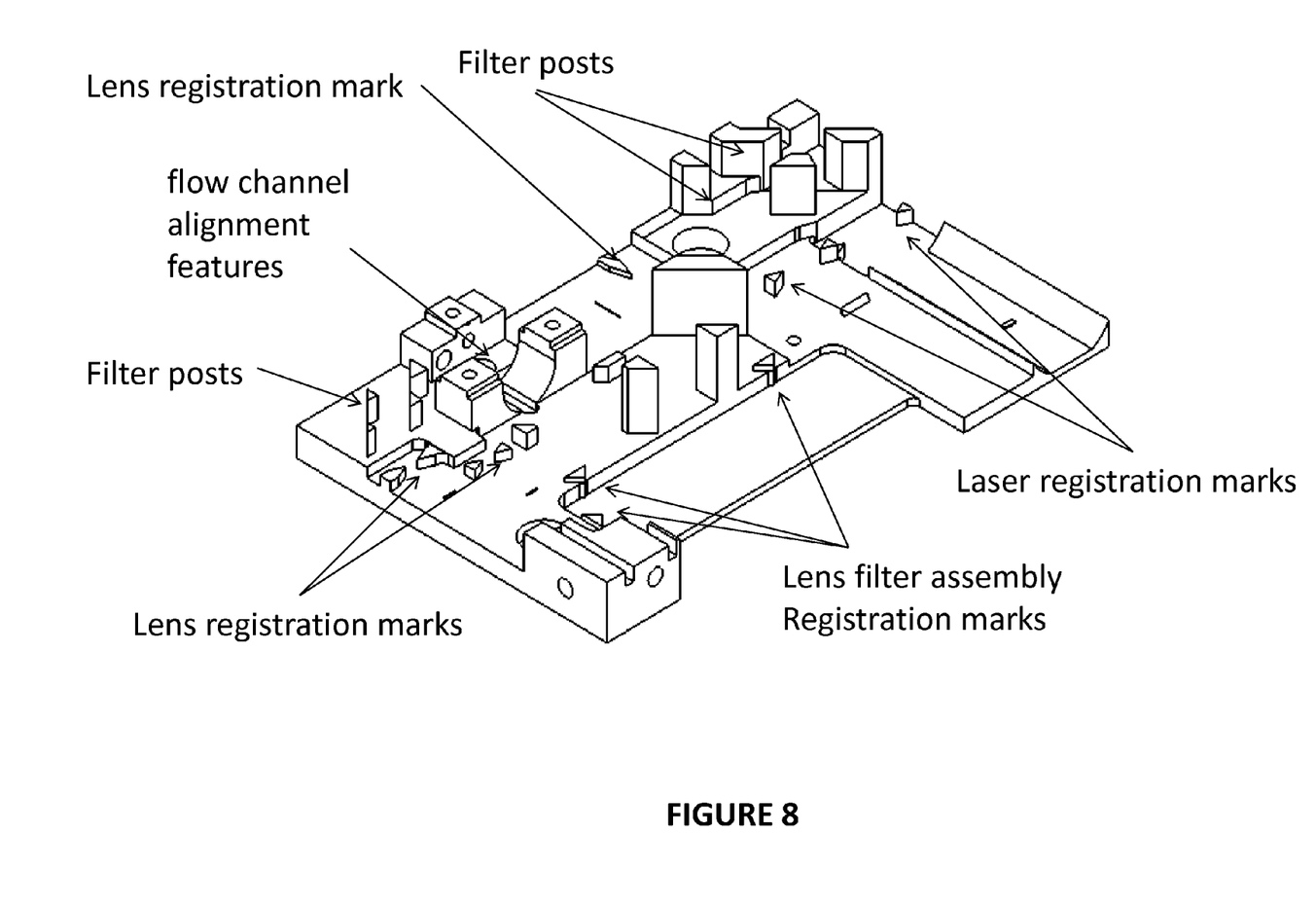
FIG. 8 shows the first embodiment of the optical block without the assembled components.

FIG. 8 shows the optical block without the assembled components. In particular, the registration features are highlighted. These allow for precise alignment of the components for large-scale manufacturing. This includes registration marks for the lasers, filters, focusing lenses, flow channel, and lens filter assembly.

Optical Block with Ports

In a second embodiment, the optical block utilizes ports instead of an open air design to accurately position the optical components. The ports are cylindrical in nature and accept cylindrical detectors, lasers, and other components. The ports assist in the alignment and positioning of the optical components. The registration features in the optical block therefore can be a different geometry than that of the open-air design. The second embodiment also has a dovetail slot for accepting a flow channel that has the reciprocal dovetail. This embodiment describes different approaches to developing a small integrated optical system.

Figure 9:
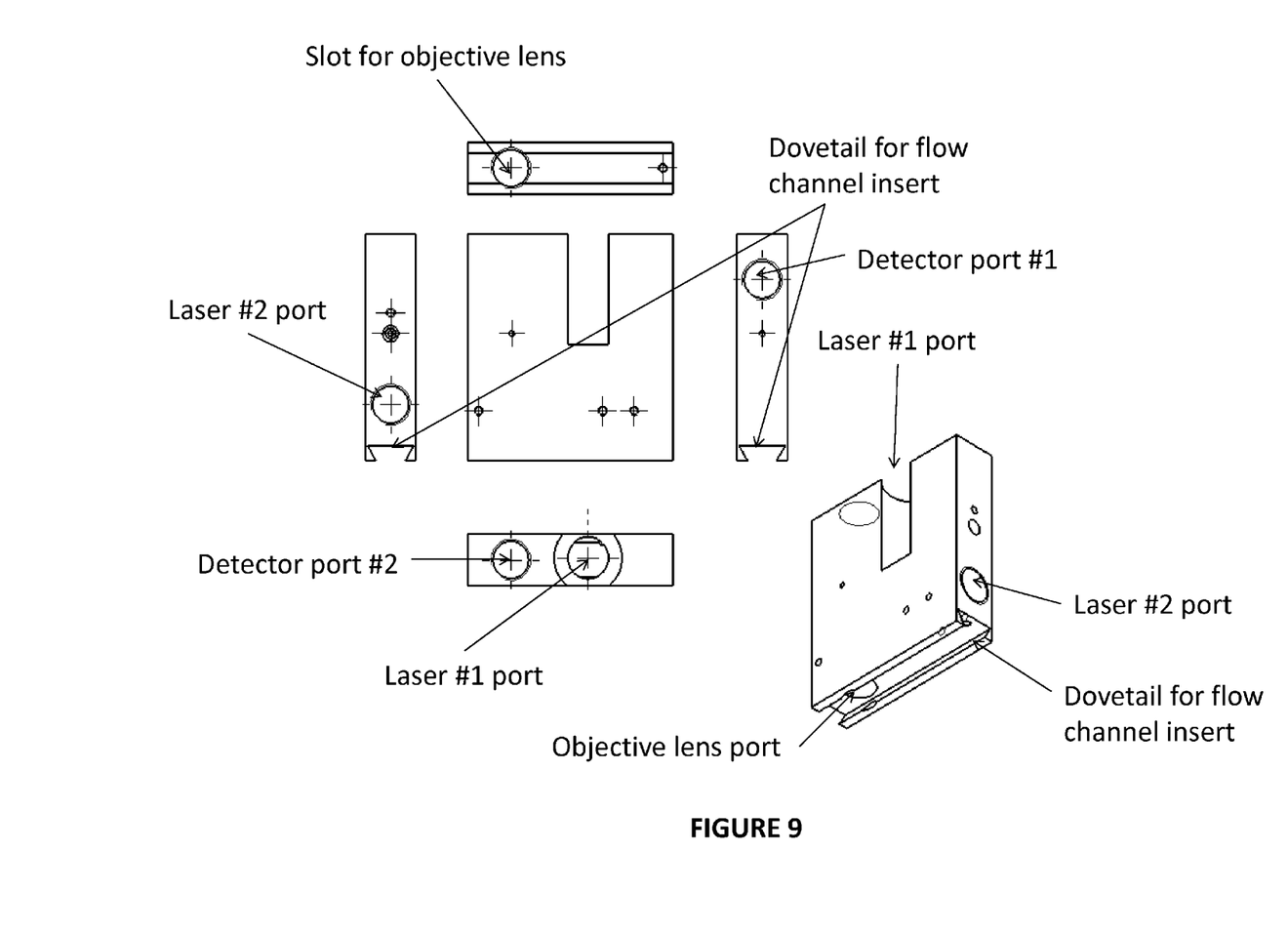
FIG. 9 shows a second embodiment of the optical block.

FIG. 9 shows the second embodiment of the optical block. It utilizes different methods of registering components. For instance, the lasers are put into circular ports. A flow channel mounted on a dovetail insert is inserted into the mating location. There are two detector ports.

Figure 10:
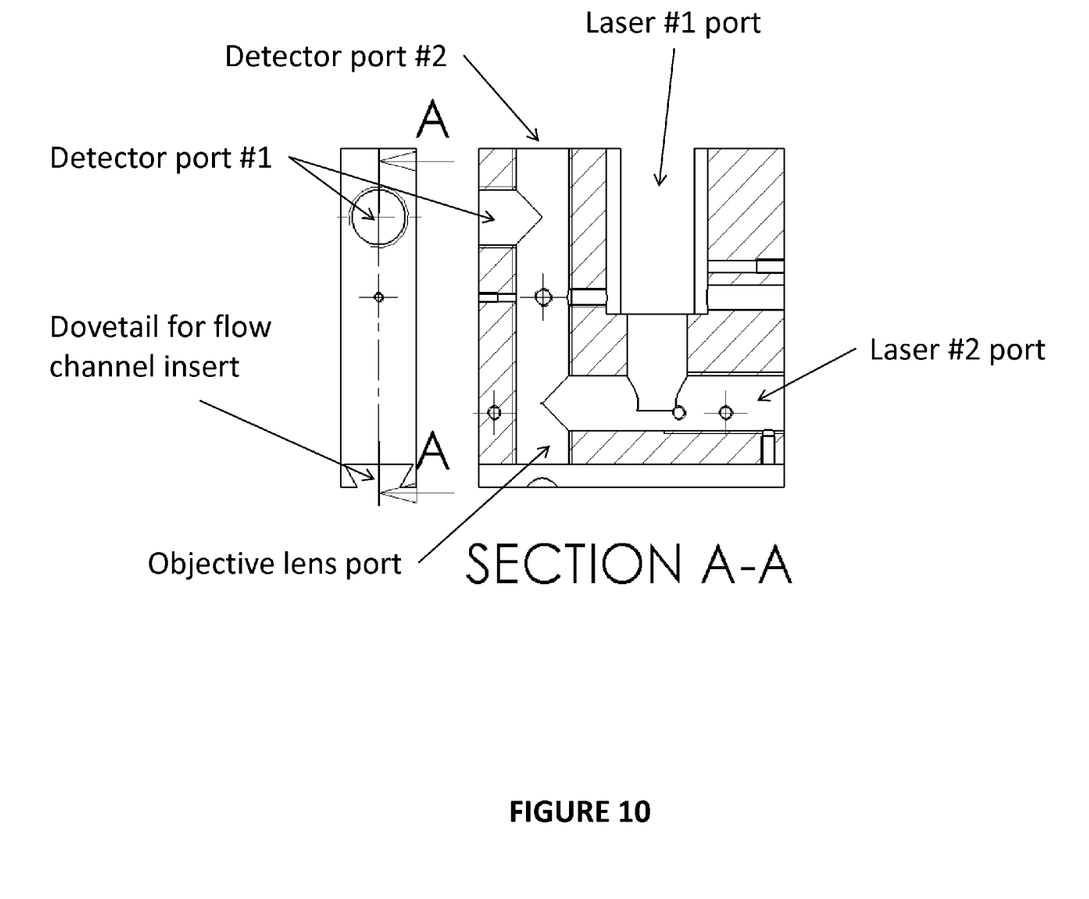
FIG. 10 is a section view of the second embodiment of the optical block.

FIG. 10 shows a section view of a second embodiment of the optical block. In particular, the registration features are defined as circular ports and a dovetail for the flow channel insert. The ports are utilized for the lasers and detectors.

Optical Block with Recesses

In a third embodiment, the optical block has precisely defined slots and receptacles for filters, filter holders, and other optical components. For instance, the dichroic filter holder and the filter cube have complementary recesses that allow for insertion and removal of the components readily. The circular ports allow for positioning of the lasers and also the detectors. In addition, this version has an integrated heat sink with the metal block.

Figure 11:
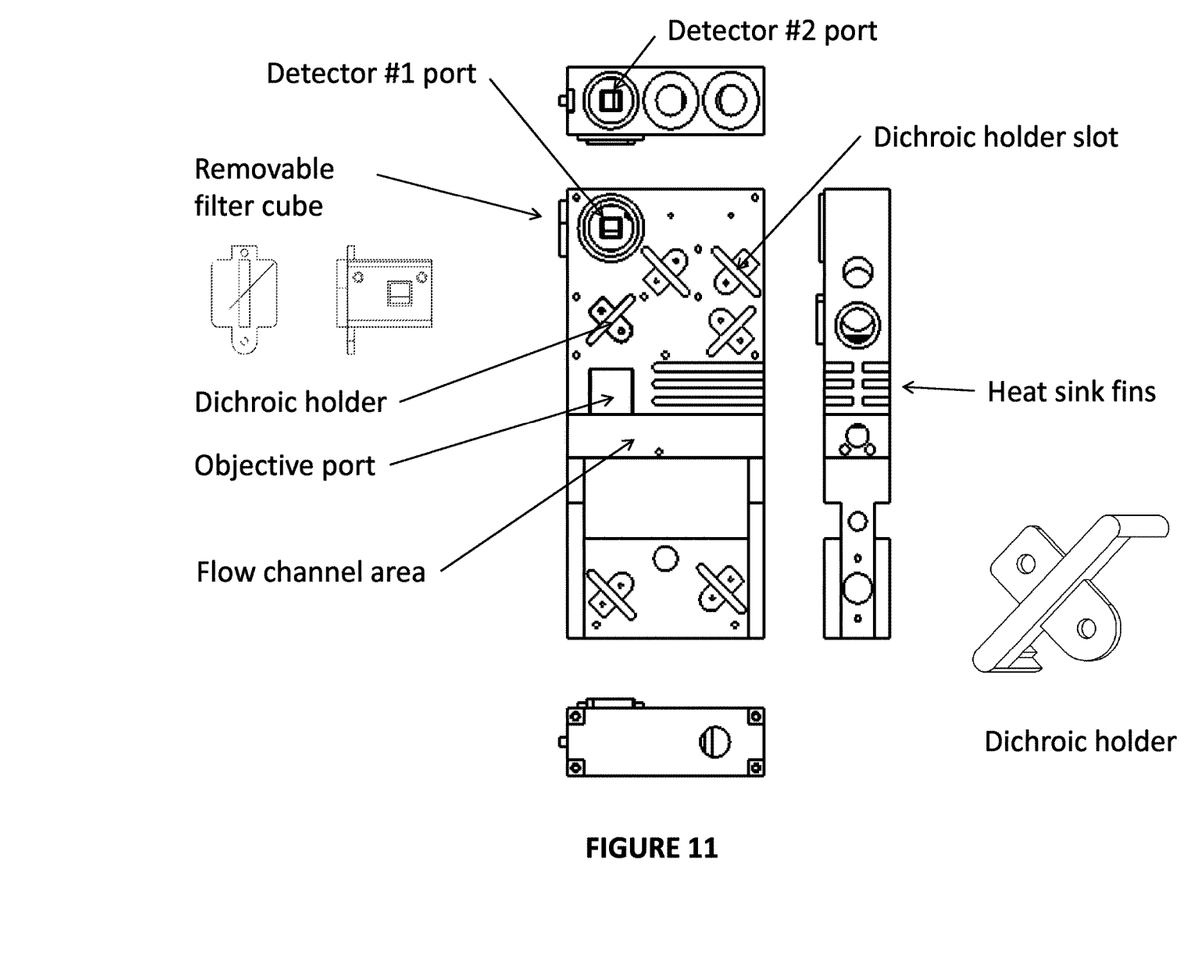
FIG. 11 shows a third embodiment of an optical block utilizing the principles of port alignment and registration.

FIG. 11 shows a third embodiment of an optical block utilizing the principles of port alignment and registration. There are two detector ports, dichroic filter slots, filter cube slot, objective port, and areas for the flow channel and heat sink.

Figure 12:
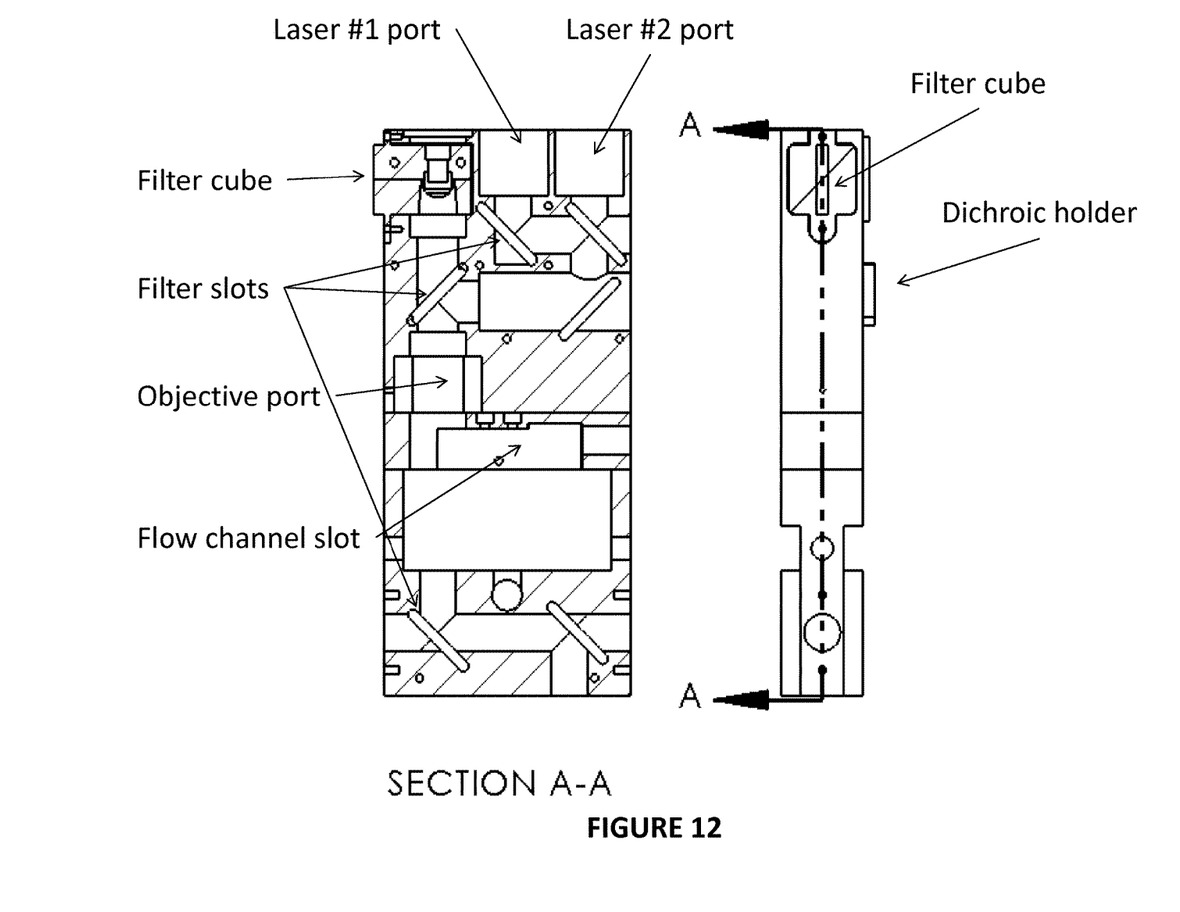
FIG. 12 is a section view of the third embodiment of the optical block.

FIG. 12 shows a section view of the third embodiment of the optical block. The section view shows the two laser ports, filter slots, objective ports, and filter cube. The slots and the ports allow for precise registration of the optical components.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. An optical block, the block comprising:
  a monolithic body that is approximately the size of a matchbox fabricated from a rigid material, the monolithic body comprising at least one registration feature fabricated from the monolithic body; and
  at least one optical component mounted within the body, using at least one registration feature.

2. The optical block of claim 1, wherein the rigid material is aluminum.

3. The optical block of claim 1, wherein the at least one optical component is selected from the group consisting of a laser, a filter, a focusing lens, a flow channel, and a detector.

4. The optical block of claim 1, wherein the registration feature is selected from the group consisting of three point alignment machined directly into the body, posts designed into the body, cylindrical ports designed into the body, and registration features on the body.

5. The optical block of claim 3, wherein the block comprises two lenses, and one of the lenses is a diverging cylindrical lens and the other lens is selected from the group consisting of a focusing achromatic lens, an aspheric lens, a plane convex lens, and a double convex lens.

6. The optical block of claim 3, wherein the block comprises two cross-cylindrical diverging lenses and a focusing lens.

7. The optical block of claim 3, wherein the block comprises tubing connection ports fabricated from hypodermic tubing.

8. The optical block of claim 1, wherein the block further comprises a sample tube port, a sheath tube port, and a burp tube port.

9. The optical block of claim 1 comprising a detector, wherein the detector is a solid-state detector.

10. The optical block of claim 9, wherein the solid-state detector is soldered directly to an electronics board.

11. The optical block of claim 9, wherein the optical block lacks a pinhole in proximity to the solid-state detector.

12. The optical block of claim 1, wherein the block further comprises an integrated heat sink.

* * * * *